(12) United States Patent
Lui et al.

(10) Patent No.: US 8,680,285 B2
(45) Date of Patent: Mar. 25, 2014

(54) METHOD FOR PRODUCING ENAMINOCARBONYL COMPOUNDS

(75) Inventors: Norbert Lui, Odenthal (DE);
Jens-Dietmar Heinrich, Burscheid (DE)

(73) Assignee: Bayer Cropscience AG, Monheim (DE)

( * ) Notice: Subject to any disclaimer, the term of this patent is extended or adjusted under 35 U.S.C. 154(b) by 138 days.

(21) Appl. No.: 13/256,607

(22) PCT Filed: Mar. 12, 2010

(86) PCT No.: PCT/EP2010/001577
§ 371 (c)(1),
(2), (4) Date: Sep. 30, 2011

(87) PCT Pub. No.: WO2010/105779
PCT Pub. Date: Sep. 23, 2010

(65) Prior Publication Data
US 2012/0016132 A1    Jan. 19, 2012

(30) Foreign Application Priority Data
Mar. 16, 2009    (EP) .................................... 09155202

(51) Int. Cl.
*C07D 405/12* (2006.01)
(52) U.S. Cl.
USPC ...................................................... 546/284.4
(58) Field of Classification Search
USPC ...................................................... 546/284.4
See application file for complete search history.

(56) References Cited

U.S. PATENT DOCUMENTS

| | | | |
|---|---|---|---|
| RE28,242 | E | 11/1974 | Boosen et al. |
| 4,555,512 | A | 11/1985 | Goldmann et al. |
| 5,905,090 | A | 5/1999 | Bertolini et al. |
| 2009/0247551 | A1 | 10/2009 | Jeschke et al. |
| 2009/0253749 | A1 | 10/2009 | Jeschke et al. |
| 2010/0190990 | A1 | 7/2010 | Lui et al. |
| 2010/0240705 | A1 | 9/2010 | Jeschke et al. |

FOREIGN PATENT DOCUMENTS

| | | |
|---|---|---|
| CA | 1 225 094 | 8/1987 |
| CH | 503 722 | 4/1971 |
| EP | 0 123 095 | 10/1984 |
| EP | 0 153 615 | 9/1985 |
| EP | 0 539 588 | 5/1993 |
| EP | 2 042 496 | 4/2009 |
| WO | 93/22305 | 11/1993 |
| WO | 99/38846 | 8/1999 |
| WO | 2007/115643 | 10/2007 |
| WO | 2007/115644 | 10/2007 |
| WO | 2007/115646 | 10/2007 |
| WO | 2009/036899 | 3/2009 |

OTHER PUBLICATIONS

Dorwald, Side Reactions in Organic Synthesis, 2005, Wiley: VCH Weinheim Preface, pp. 1-15 & Chapter 8, pp. 279-308.*

International Search Report of PCT/EP2010/001577 Mailed Sep. 6, 2010.
European Search Report of EP09155202, Completed Sep. 30, 2009.
Greenhill et al., "A New and Easier Route to Tetronic Acid," Tetrahedron Letters No. 31, pp. 2683-2684, (1974).
Schmidt et al., "A Convenient Synthesis of 2,4(3H,5H)-Furandione (B-Tetronic Acid)1a," Synthetic Communications, vol. 11, No. 5, pp. 385-390, (1981).
Bertolini et al., "A New Rational Hypothesis for the Pharmacophore of the Active Metabolite of Leflunomide, A Potent Immunosuppressive Drug," J. Med. Chem., vol. 40, pp. 2011-2016, (1997).
Mack et al., "On the Mechanism of a Novel 3(2H)-Furanone-2(5H)-Furanone Rearrangement," J. Heterocyclic Chem., vol. 25, pp. 603-606, (1988).
Shanadala et al. "Reaction of Methyl Tetronate With Some Amines, Synthesis of Substituted 4-Aminobut-2-Enolides," J. Heterocyclic Chem., vol. 21, pp. 1753-1754, (1984).
Mulholland et al., "A Synthesis of Tetronic Acid [Furan-2(3H,4(5H)-Dione] and Three Analogues," J. Chem. Soc. Perkin Trans. 1, vol. 1, No. 9/10, pp. 1225-1231, (1972).
Momose et al., "2(3H)- and 2(5H)-Furanones. III.," Heterocycles, vol. 27, No. 8, pp. 1907-1923, (1988).

(Continued)

*Primary Examiner* — Patricia L Morris
(74) *Attorney, Agent, or Firm* — Miles & Stockbridge P.C.

(57) ABSTRACT

The present invention relates to a process for the preparation of enaminocarbonyl compounds of the formula (I)

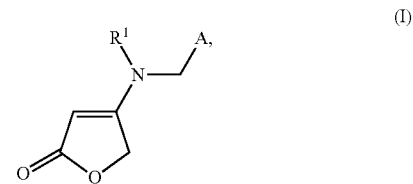

(I)

where compounds of the formula (II)

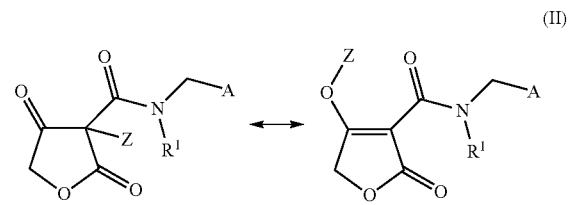

(II)

are reacted in the presence of a Brønsted acid to give compounds of the formula (I), and A, R1 and Z are as defined in the description, and also corresponding starting compounds which are used in the process according to the invention.

8 Claims, No Drawings

(56) References Cited

OTHER PUBLICATIONS

St. Georgiev et al., "Drug-Induced Modification of the Immune Response 4-(Arylamino)-2,5-Dihydro-2-oxo-N-(Trans-2-Phenylcyclopropyl)Furan-3-Carboxamides as Novel Antiallergic Compounds," Helvetica Chimica Acta, vol. 70, pp. 1526-1530, (1987).

Benary, "Ueber Die Einwirkung von Chloracetylchlorid auf Malonester und Ueber Imido-tetronaeure," Berichte der Deutchen Chemischen Gesellschaft, vol. 45, pp. 3682-3686, (1912).

Anschuetz, "Ueber Imido-Tetronsauure," Berichte der Deutchen Chemischen Gesellschaft, vol. 45, pp. 2374-2378, (1912).

Borsche et al., "Ueber Einige Neue Derivate des Diphenylenoxyds," Berichte der Deutchen Chemischen Gesellschaft, vol. 41, pp. 1940-1944, (1908).

* cited by examiner

METHOD FOR PRODUCING ENAMINOCARBONYL COMPOUNDS

CROSS REFERENCE TO RELATED APPLICATIONS

This application is a §371 National Stage Application of PCT/EP2010/001577, filed Mar. 12, 2010, which claims priority to European Application No. 09155202.6, filed Mar. 16, 2009.

BACKGROUND OF THE INVENTION

1. Field of the Invention

The present invention relates to a process for the preparation of 4-aminobut-2-enolides.

2. Description of Related Art

Certain substituted enaminocarbonyl compounds are known as insecticidally active compounds from EP 0 539 588 A1. Moreover, the International Patent Applications WO 2007/115644, WO 2007/115643 and WO 2007/115646 describe corresponding insecticidally active enaminocarbonyl compounds.

In general, enaminocarbonyl compounds are synthesized from tetronic acid and an amine according to Scheme 1 below. This procedure is described, for example, in EP 0 539 588 A1, and also in Heterocycles Vol. 27, No. 8, pages 1907 to 1923 (1988).

Scheme 1:

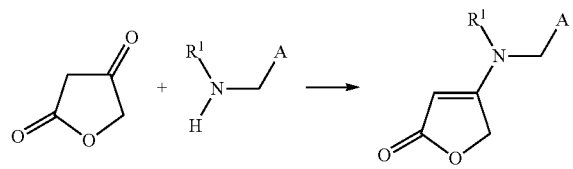

A disadvantage of this process is in particular that anhydrous tetronic acid is required as starting compound, the production of which is complex and cost-intensive.

For example, tetronic acid is generally prepared starting from acetoacetic ester via a bromination and subsequent hydrogenation (cf. Synthetic Communication, 11(5), pages 385 to 390 (1981)). The total yield of tetronic acid starting from acetoacetic ester is less than 40% here, which does not make the process very attractive from an industrial point of view.

CH Patent 503 722 describes a further process for the preparation of tetronic acid. In this process, 4-chloroacetoacetic ester is reacted with an aromatic amine to give 3-arylaminocrotonolactone and then the tetronic acid is released through treatment with mineral acids. The disadvantage of this process is that the isolation of the tetronic acid is only possible by means of high-vacuum sublimation, which also does not make this process very attractive from an industrial point of view.

A further process for the preparation of tetronic acid is described in EP 0 153 615 A, in which the starting material is 2,4-dichloroacetoacetic ester. This likewise multistage and complex process produces the desired compound likewise only in a moderate overall yield of 65%.

Tetrahedron Letters, No. 31, pages 2683 and 2684 (1974) describes the preparation of tetronic acid and a corresponding enaminocarbonyl compound. The synthesis described therein is given in Scheme 2 below. The starting material used here is the dimethyl ester of acetylenedicarboxylic acid.

Scheme 2:

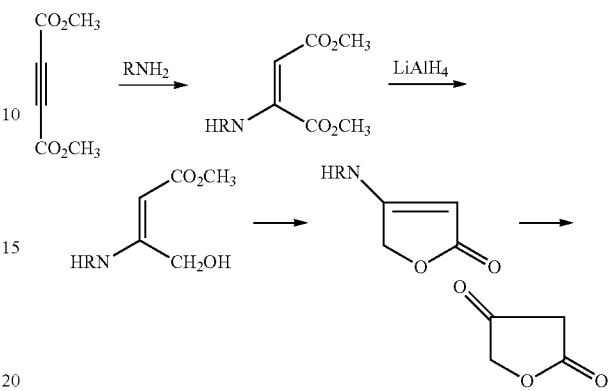

A disadvantage of this process is the low overall yield of only 30% and also the requirement of having to use cost-intensive starting materials, for example lithium aluminium hydride ($LiAlH_4$), as reagents.

Furthermore, a process for the preparation of enaminocarbonyl compounds starting from methyl tetronate is known from the prior art (J. Heterocyclic Chem., 21, 1753 (1984)). For this process, the starting material used is the cost-intensive ester of 4-bromo-3-methoxybut-3-enecarboxylic acid.

A further process starts from a 4-chloroacetoacetic ester, which is reacted with amines (Heterocycles, Vol. 27, No. 8, 1988, pages 1907 to 1923). The reaction to give the aminofuran is carried out in one step. Here, the amine is added with glacial acetic acid to a solution of 4-chloroacetoacetic ester in benzene and the resulting mixture is heated under reflux for several hours. The yields of 4-methylamino-2(5H)-furanone in this synthesis are only 40%.

EP 0 123 095 A discloses a process in which tetronamide is prepared from 3-amino-4-acetoxycrotonic ester. 3-Amino-4-acetoxycrotonic ester is cost-intensive and complex to prepare, and so an economic synthesis by means of this process is not possible.

A further process for the preparation of tetronic acid starting from malonic esters and chloroacetyl chloride is known from J. Chem. Soc., Perkin Trans. 1 (1972), No. 9/10, pages 1225 to 1231. This process produces the desired target compound with a yield of only 43%.

The aforementioned International Patent Application WO 2007/115644 describes the preparation of enaminocarbonyl compounds, for example of 4-[[(6-chloropyridin-3-yl)methyl](3,3-dichloro-prop-2-en-1-yl)amino]furan-2(5H)-one by reacting 4-[[(6-chloropyridin-3-yl)methyl]amino]furan-2 (5H)-one with 3-bromo-1,1-dichloroprop-1-ene (cf. Preparation Example, Process 2, Example (3)). WO 2007/115644 also describes the preparation of enaminocarbonyl compounds, for example of 4-[[(6-chloropyridin-3-yl)methyl](2-fluoroethyl)amino]furan-2(5H)-one by reacting 4-[[(2-fluoroethyl)amino]furan-2(5H)-one with 2-chloro-5-chloromethylpyridine (cf. Preparation Examples, Process 3, Example (4)). The reactions are preferably carried out with hydrides of lithium or sodium. These substrates are generally cost-intensive and at the same time can only be handled with difficulty for reasons of safety.

In WO 2009/036899, which claims the priority of the European Patent Application No. 07116639, enaminocarbonyl compounds are prepared, for example, starting from 4-(methoxycarbonyl)-5-oxo-2,5-dihydrofuran-3-ol and an amine.

Scheme 3:

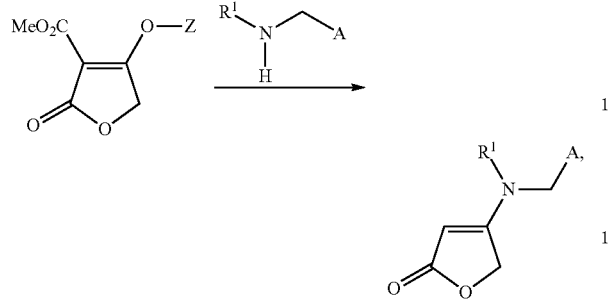

where
R$^1$ is hydrogen, alkyl, haloalkyl, alkenyl, haloalkenyl, alkynyl, cycloalkyl, cycloalkylalkyl, halocycloalkyl, alkoxy, alkyloxyalkyl, halocycloalkylalkyl or arylalkyl;

Z is hydrogen, alkali metal or alkaline earth metal; and

A is pyrid-2-yl or pyrid-4-yl or is pyrid-3-yl which is optionally substituted in position 6 by fluorine, chlorine, bromine, methyl, trifluoromethyl or trifluoromethoxy, or is pyridazin-3-yl which is optionally substituted in position 6 by chlorine or methyl, or is pyrazin-3-yl or is 2-chloropyrazin-5-yl or is 1,3-thiazol-5-yl which is optionally substituted in position 2 by chlorine or methyl, or is pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl which is optionally substituted by fluorine, chlorine, bromine, cyano, nitro, C$_1$-C$_4$-alkyl (which is optionally substituted by fluorine and/or chlorine), C$_1$-C$_3$-alkylthio (which is optionally substituted by fluorine and/or chlorine), or C$_1$-C$_3$-alkylsulphonyl (which is optionally substituted by fluorine and/or chlorine), or is

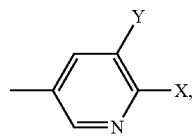

in which
X is halogen, alkyl or haloalkyl and
Y is halogen, alkyl, haloalkyl, haloalkoxy, azido or cyano.

SUMMARY OF THE INVENTION

Proceeding from this prior art, the object of the present invention is to provide an alternative process for the preparation of enaminocarbonyl compounds which is preferably easy and cost-effective to carry out. The enaminocarbonyl compounds obtainable using the desired process should here preferably be obtained in high yield and high purity. In particular, the desired process should allow the desired target compounds to be obtained without the need for complex purification methods.

This object is achieved by a novel process for the preparation of enaminocarbonyl compounds of the general formula (I):

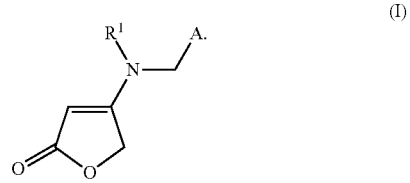

The process according to the invention is characterized in that compounds of the general formula (II)

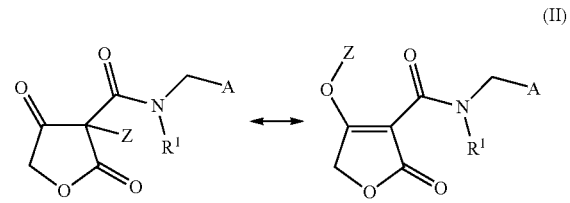

are reacted to give compounds of the formula (I), where
R$^1$ is hydrogen, alkyl, haloalkyl, alkenyl, haloalkenyl, alkynyl, cycloalkyl, cycloalkylalkyl, halocycloalkyl, alkoxy, alkyloxyalkyl, halocycloalkylalkyl, aryl or arylalkyl;

Z is hydrogen, alkali metal or alkaline earth metal; and

A is pyrid-2-yl or pyrid-4-yl or is pyrid-3-yl which is optionally substituted in position 6 by fluorine, chlorine, bromine, methyl, trifluoromethyl or trifluoromethoxy, or is pyridazin-3-yl which is optionally substituted in position 6 by chlorine or methyl, or is pyrazin-3-yl or is 2-chloropyrazin-5-yl or is 1,3-thiazol-5-yl which is optionally substituted in position 2 by chlorine or methyl, or is pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl which is optionally substituted by fluorine, chlorine, bromine, cyano, nitro, C$_1$-C$_4$-alkyl (which is optionally substituted by fluorine and/or chlorine), C$_1$-C$_3$-alkylthio (which is optionally substituted by fluorine and/or chlorine), or C$_1$-C$_3$-alkylsulphonyl (which is optionally substituted by fluorine and/or chlorine), or is

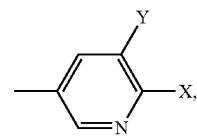

where
X is halogen, alkyl or haloalkyl and
Y is halogen, alkyl, haloalkyl, haloalkoxy, azido or cyano.

According to the invention, it is thus envisaged that the desired enaminocarbonyl compounds of the general formula (I) are prepared by reacting the corresponding compounds of the general formula (II). The desired enaminocarbonyl compounds of the general formula (I) are obtained under the reaction conditions that are in accordance with the invention and preferred reaction conditions that are specified below with good yields in high purity, as a result of which the process according to the invention overcomes the aforementioned disadvantages of the prior art processes. The desired compounds are obtained here in a purity which generally does not necessitate extensive work-up of the direct reaction product.

DETAILED DESCRIPTION OF A PREFERRED EMBODIMENT

Preferred, particularly preferred and very particularly preferred meanings of the radical A and $R^1$ listed in the aforementioned general formulae (I) and (II) are explained below.

A is preferably selected from the group consisting of 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl and 5-difluoromethyl-6-iodopyrid-3-yl.

$R^1$ is preferably selected from hydrogen, alkyl, haloalkyl, alkenyl, haloalkenyl, alkynyl, cycloalkyl, cycloalkylalkyl, halocycloalkyl, halocycloalkylalkyl and alkoxyalkyl.

Z is preferably selected from the group consisting of alkali metals and hydrogen;

A is particularly preferably selected from the group consisting of 6-fluoropyrid-3-yl, 6-chloropyrid-3-yl, 6-bromopyrid-3-yl, 6-chloro-1,4-pyridazin-3-yl, 2-chloro-1,3-thiazol-5-yl, 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl and 5-difluoromethyl-6-chloropyrid-3-yl.

$R^1$ is particularly preferably selected from the group consisting of methyl, ethyl, propyl, vinyl, allyl, propargyl, cyclopropyl, alkoxyalkyl, 2-fluoroethyl, 2,2-difluoroethyl and 2-fluoro-cyclopropyl.

Z is particularly preferably selected from the group consisting of hydrogen, sodium and potassium;

A is very particularly preferably selected from the group consisting of 6-chloropyrid-3-yl, 6-bromopyrid-3-yl, 6-chloro-1,4-pyridazin-3-yl, 2-chloro-1,3-thiazol-5-yl, 5-fluoro-6-chloropyrid-3-yl and 5-fluoro-6-bromopyrid-3-yl.

$R^1$ is very particularly preferably selected from the group consisting of methyl, ethyl, n-propyl, n-prop-2-enyl, n-prop-2-inyl, cyclopropyl, methoxyethyl, 2-fluoroethyl and 2,2-difluoroethyl.

Z is very particularly preferably selected from the group consisting of sodium and hydrogen.

In one preferred embodiment of the present invention, in the process according to the invention, starting compounds of the general formula (II) are used in which the substituents A, Z and $R^1$ have the aforementioned preferred meanings, it being possible for the preferred, particularly preferred and very preferred meanings of the substituents to be combined.

In one particularly preferred embodiment of the present invention, in the process according to the invention, starting compounds of the general formula (II) are used in which the substituents A, Z and $R^1$ have the aforementioned particularly preferred meanings, it being possible for the preferred, particularly preferred and very preferred meanings of the substituents to be combined.

In one very particularly preferred embodiment of the present invention, in the process according to the invention, starting compounds of the general formula (II) are used in which the substituents A, Z and $R^1$ have the aforementioned very particularly preferred meanings, it being possible for the preferred, particularly preferred and very preferred meanings of the substituents to be combined.

Within the context of the present invention—irrespective of the individual aforementioned preferred, particularly preferred and very particularly preferred meanings—the following meaning is generally attributed to the individual radicals used:

Unless mentioned otherwise, the term "alkyl", either on its own or in combination with further terms such as, for example, haloalkyl, alkoxyalkyl, cycloalkylalkyl, halocycloalkylalkyl and arylalkyl, is understood as meaning within the context of the present invention a radical of a saturated, aliphatic hydrocarbon group having 1 to 12 carbon atoms, which may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. Of these alkyl radicals, $C_1$-$C_6$-alkyl radicals are particularly preferred. $C_1$-$C_4$-alkyl radicals are especially preferred, specifically methyl and ethyl.

Unless mentioned otherwise, the term "alkenyl", either on its own or in combination with further terms, is understood according to the invention as meaning a linear or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl. Of these, preference is given to $C_2$-$C_6$-alkenyl radicals and particular preference is given to $C_2$-$C_4$-alkenyl radicals.

Unless mentioned otherwise, the term "alkynyl", either on its own or in combination with further terms, is understood according to the invention as meaning a linear or branched $C_2$-$C_{12}$-alkynyl radical which has at least one triple bond, for example ethynyl, 1-propynyl and propargyl. Of these, preference is given to $C_3$-$C_6$-alkynyl radicals and particular preference is given to $C_3$-$C_4$-alkynyl radicals. The alkynyl radical here may also have at least one double bond.

Unless mentioned otherwise, the term "cycloalkyl", either on its own or in combination with further terms, is understood according to the invention as meaning a $C_3$-$C_8$-cycloalkyl radical, for example cyclopropyl, cyclobutyl, cyclopentyl, cyclohexyl, cycloheptyl and cyclooctyl. Of these, preference is given to $C_3$-$C_6$-cycloalkyl radicals.

Unless mentioned otherwise, the term "aryl" is understood according to the invention as meaning an aromatic radical have 6 to 14 carbon atoms, preferably phenyl.

Unless mentioned otherwise, the term "arylalkyl" is understood as meaning a combination of radicals "aryl" and "alkyl" defined according to the invention, where the radical is generally bonded via the alkyl group. Examples thereof are benzyl, phenylethyl or α-methylbenzyl, with benzyl being particularly preferred.

Unless mentioned otherwise, the term "radicals substituted by halogen", for example haloalkyl, is understood as meaning radicals halogenated one or more times up to the maximum possible number of substituents. In the case of multiple halogenation, the halogen atoms may be identical or different. Halogen here is fluorine, chlorine, bromine or iodine, in particular fluorine, chlorine or bromine.

Unless mentioned otherwise, the term "alkoxy", either on its own or in combination with further terms such as, for example, haloalkoxy, is presently understood as meaning a radical O-alkyl, where the term "alkyl" has the aforementioned meaning.

Optionally substituted radicals may be substituted one or more times, where, in the case of a multiple substitution, the substituents may be identical or different.

The present invention further provides compounds of the formula (II)

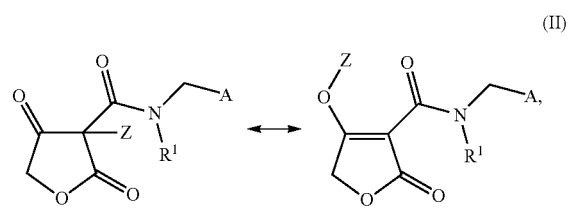

(II)

in which the radicals A, Z and R$^1$ are as defined above.

The synthesis of corresponding modified derivatives of the compounds of the general formula (II) can be carried out in accordance with Scheme 4 below, for example starting from 2,4-dioxotetrahydrofuran-3-carboxylates of the general formula (IV) with amines of the formula (III) or in accordance with literature (Bertolini et al., J. Med. Chem. 1997, 40, 2011-2016, Benary, Ber., 1908, 41, 1943.):

Scheme 4:

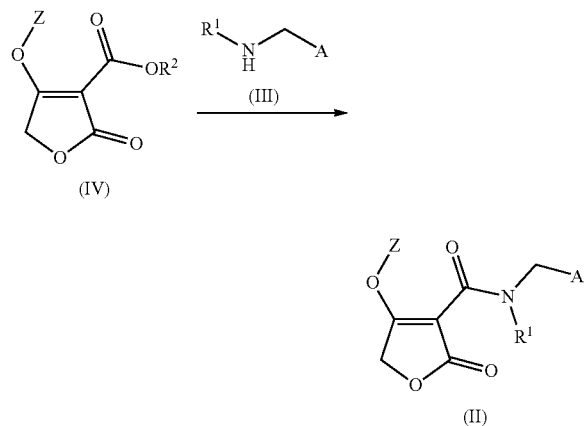

where the radicals A, Z and R$^1$ are as defined above and R$^2$ is alkyl, aryl or arylalkyl.

The compound (II) may also be present in an isomer form.

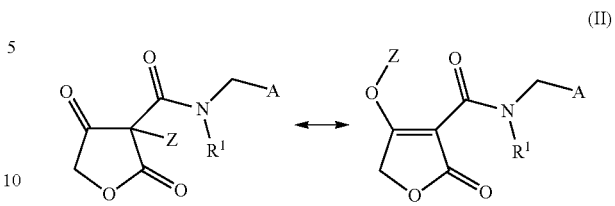

(II)

The 2,4-dioxotetrahydrofuran-3-carboxylates of the general formula (IV) used as starting materials can be prepared by processes known from the prior art (R. Anschütz, Ber., 1912, 45, 2374; E. Benary, Ber., 1912, 45, 3682). The amines of the general formula (III) are commercially available or can be prepared by processes known in the literature (cf. e.g. S. Patai "The Chemistry of Amino Group", Interscience Publishers, New York, 1968).

The reaction according to the invention, shown above, of the compounds of the general formula (II) to compounds of the general formula (I) is carried out in the presence of solvents (diluents). Solvents are advantageously used in an amount such that the reaction mixture remains readily stirrable throughout the entire process. Suitable solvents for carrying out the process according to the invention are all organic solvents that are inert under the reaction conditions.

Examples include: halogenated hydrocarbons, in particular chlorinated hydrocarbons, such as tetrachloroethylene, tetrachloroethane, dichloropropane, methylene chloride, dichlorobutane, chloroform, tetrachloromethane, trichloroethane, trichloroethylene, pentachloroethane, difluorobenzene, 1,2-dichloroethane, chlorobenzene, bromobenzene, dichlorobenzene, chlorotoluene, trichlorobenzene; ethers, such as ethyl propyl ether, methyl tert-butyl ether, n-butyl ether, anisole, phenetol, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether; methyl-THF and polyethers of ethylene oxide and/or propylene oxide; nitrohydrocarbons such as nitromethane, nitroethane, nitropropane, nitrobenzene, chloronitrobenzene, o-nitrotoluene; nitriles such as acetonitrile, propionitrile, butyronitrile, isobutyronitrile, benzonitrile, phenylnitrile, m-chlorobenzonitrile, and also compounds such as tetrahydrothiophene dioxide and dimethyl sulphoxide, tetramethylene sulphoxide, dipropyl sulphoxide, benzylmethyl sulphoxide, diisobutyl sulphoxide, dibutyl sulphoxide, diisoamyl sulphoxide; sulphones such as dimethyl sulphone, diethyl sulphone, dipropyl sulphone, dibutyl sulphone, diphenyl sulphone, dihexyl sulphone, methylethyl sulphone, ethylpropyl sulphone, ethylisobutyl sulphone and pentamethylene sulphone; aliphatic, cycloaliphatic or aromatic hydrocarbons such as pentane, n-hexane, n-heptane, n-octane, nonane, for example so-called white spirits with components having boiling points in the range for example from 40° C. to 250° C., cymene, benzine fractions within a boiling interval from 70° C. to 190° C., cyclohexane, methylcyclohexane, petroleum ether, ligroin, octane, benzene, toluene, xylene; esters such as methyl acetate, ethyl acetate, butyl acetate, isobutyl acetate, and also dimethyl carbonate, dibutyl carbonate, ethylene carbonate; amides such as hexamethylenephosphortriamide, formamide, N,N-dimethylacetamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine; and aliphatic alcohols, such as methanol, ethanol, n-propanol and isopropanol and n-butanol.

The reaction according to the invention is preferably carried out in a solvent which is selected from the group consisting of dioxane, butyronitrile, propionitrile, acetonitrile, DME, toluene, methyl-THF, dichlorobenzene, chlorobenzene, n-heptane, isobutanol, n-butanol, ethanol, methyl tert-butyl ether, isopropyl ethyl ether and mixtures thereof.

The reaction can also be carried out in the presence of water.

The reaction of the compounds of the general formula (II) is preferably carried out in the presence of a Brønsted acid.

The molar ratio of the Brønsted acid and the amines of the formula (III) may vary. The ratio of the Brønsted acid to the amine of formula (III) preferably lies in the range of approximately 10:0.6 to approximately 1:1.5, particularly in the range of approximately 5:0.9 to 1:1.2, more particularly in the range of approximately 2:1 to approximately 1:1.1.

In this connection, it is possible to use either organic or inorganic Brønsted acids. Preferably, inorganic acids are used, for example phosphoric acid ($H_3PO_4$), sulphuric acid ($H_2SO_4$), hydrochloric acid (HCl), hydrobromic acid (HBr), hydrofluoric acid (HF) or potassium hydrogensulphate ($KHSO_4$). The individual acids can be used here either in anhydrous form or in hydrous form, for example as 85% strength phosphoric acid or 37% strength hydrochloric acid, i.e. especially in forms in which the acids are commercially available. Examples of suitable organic acids are trifluoroacetic acid, acetic acid, methanesulphonic acid and p-toluenesulphonic acid. Of the aforementioned acids, preference is given in particular to phosphoric acid, sulphuric acid, potassium hydrogensulphate and trifluoroacetic acid.

The reaction for the preparation of the compounds of the general formula (I) can generally be carried out at subatmospheric pressure, at atmospheric pressure or at superatmospheric pressure. The temperatures used can likewise vary, depending on the substrates used, and are easy to ascertain for the person skilled in the art through routine experiments. For example, the reaction for the preparation of the compounds of the general formula (I) can be carried out at a temperature of from 20 to 200° C., preferably 20 to 150° C.

At the end of the reaction, the water of reaction can be removed by distilling some of the solvent as azeotrope. In the case of high-boiling solvents, this can take place at subatmospheric pressure. Through this operation, a quantitative conversion is generally achieved.

If the reaction is carried out in a solvent, the solvent can be removed after the end of the reaction by distillation. This can take place under atmospheric pressure or reduced pressure at room temperature or elevated temperatures.

Isolation of the desired compounds of the general formula (I) can take place, for example, also by crystallization.

The present invention is illustrated by reference to the examples below, although the examples should not be interpreted in a manner which limits the invention.

PREPARATION EXAMPLES

Example 1

Preparation of 4-[[(6-chloropyridin-3-yl)methyl](2,2-difluoroethyl)amino]furan-2(5H)-one At room temperature, 0.5 g of potassium hydrogensulphate are added to a suspension of 1.7 g of N-[(6-chloropyridin-3-yl)methyl]-N-(2,2-difluoroethyl)-4-hydroxy-2-oxo-2,5-dihydrofuran-3-carboxamide in 50 ml of butyronitrile. The mixture is heated at reflux for 5 hours. It is then cooled to room temperature and washed with 30 ml of water. The solvent is removed in vacuo. This gives 1 g of 4-[[(6-chloropyridin-3-yl)methyl](2,2-difluoroethyl)amino]furan-2(5H)-one (this corresponds to 77% yield).

$^1$H-NMR (CDCl$_3$, 298K) δ: 3.53 (td, 2H), 4.52 (s, 2H), 4.82 (s, 2H), 4.83 (s, 1H), 5.96 (tt, 1H), 7.37 (d, 1H), 7.55 (dd, 1H), 8.27(d, 1H)

Example 2

Preparation of N-[(6-chloropyridin-3-yl)methyl]-N-(2,2-difluoroethyl)-4-hydroxy-2-oxo-2,5-dihydrofuran-3-carboxamide 10 g of methyl 4-hydroxy-2-oxo-2,5-dihydrofuran-3-carboxylate are initially introduced in 111 g of butyronitrile and admixed with 5 g of N-[(6-chloropyridin-3-yl)methyl]-2,2-difluoroethanamine. The solution is heated at 65° C. for 3 h. The solution is then extracted with 300 ml of water and then washed with 300 ml of 5% strength hydrochloric acid solution. The organic phase is dried over magnesium sulphate and the solvent is removed in vacuo. For purification, recrystallization from isopropanol is carried out.

NMR (CD$_3$CN): 1H (s, 8.19 ppm); 1H (d, 7.63 ppm); 1H (d, 7.24 ppm); 1H (t, 6.09 ppm); 2H (s, 4.62 ppm); 2H (s, 3.98 ppm); 2H (m, 3.62 ppm)

The invention claimed is:

1. A process for preparing a compound of formula (I)

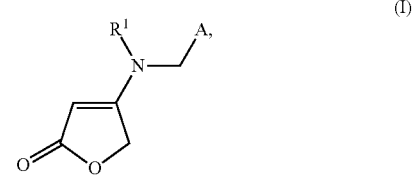

comprising reacting a compound of formula (II)

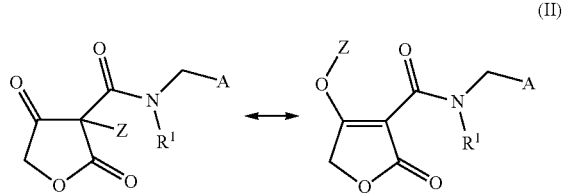

in the presence of a Brønsted acid to give a compound of formula (I),
where
$R^1$ is hydrogen, alkyl, or haloalkyl;
Z is hydrogen, alkali metal or alkaline earth metal; and
A is pyrid-2-yl or pyrid-4-yl or is pyrid-3-yl which is optionally substituted in position 6 by fluorine, chlorine, bromine, methyl, trifluoromethyl or trifluoromethoxy.

2. A process according to claim 1, wherein the Brønsted acid is selected from the group consisting of $H_3PO_4$, $H_2SO_4$, HCl, HBr, HF, $KHSO_4$, trifluoroacetic acid, acetic acid, methanesulphonic acid and p-toluenesulphonic acid.

3. A process according to claim 1, where
R$^1$ is hydrogen, C$_{1-12}$-alkyl, or C$_{1-12}$-haloalkyl.

4. A process according to claim 1, where
A is 6-fluoropyrid-3-yl, 6-chloropyrid-3-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl;
R$^1$ is methyl, ethyl, propyl, 2-fluoroethyl, or 2,2-difluoroethyl; and
Z is sodium, potassium or hydrogen.

5. A process according to claim 1, where
A is 6-chloropyrid-3-yl, 6-bromopyrid-3-yl, 5-fluoro-6-chloropyrid-3-yl or 5-fluoro-6-bromopyrid-3-yl and
R$^1$ is methyl, ethyl, n-propyl, 2-fluoroethyl or 2,2-difluoroethyl; and
Z is sodium or hydrogen.

6. A process according to claim 1, wherein the reacting is carried out in at least one solvent which is selected from the group consisting of dioxane, butyronitrile, propionitrile, acetonitrile, DME, toluene, methyl-THF, dichlorobenzene, chlorobenzene, n-heptane, isobutanol, n-butanol, ethanol, methyl tert-butyl ether, and isopropyl ethyl ether.

7. A process according to claim 1, wherein the reacting is carried out at a temperature from 20° C. to 150° C.

8. A process according to claim 1, wherein the compound of formula (I) is 4-[[(6-chloropyridin-3-yl)methyl](2,2-difluoroethyl)amino]furan-2(5H)-one.

\* \* \* \* \*